United States Patent
Roessler

(10) Patent No.: US 8,093,230 B2
(45) Date of Patent: Jan. 10, 2012

(54) SUPERSATURATED AQUEOUS IFOSFAMIDE COMPOSITIONS

(75) Inventor: Berthold Roessler, Halle (DE)

(73) Assignee: Baxter International Inc., Deerfield, IL (US)

( * ) Notice: Subject to any disclaimer, the term of this patent is extended or adjusted under 35 U.S.C. 154(b) by 420 days.

(21) Appl. No.: 10/952,027

(22) Filed: Sep. 28, 2004

(65) Prior Publication Data

US 2005/0124589 A1 Jun. 9, 2005

Related U.S. Application Data

(60) Provisional application No. 60/507,750, filed on Oct. 1, 2003.

(51) Int. Cl.
*A61K 31/665* (2006.01)

(52) U.S. Cl. ............ 514/99; 514/109; 514/110

(58) Field of Classification Search .......... 514/99, 514/109, 110
See application file for complete search history.

(56) References Cited

U.S. PATENT DOCUMENTS

| 3,732,340 A * | 5/1973 | Arnold et al. ........... 558/81 |
| 4,882,452 A | 11/1989 | Engel et al. |
| 4,959,215 A * | 9/1990 | Sauerbier et al. ........ 424/422 |
| 5,204,335 A | 4/1993 | Sauerbier et al. |
| 5,227,373 A * | 7/1993 | Alexander et al. ....... 514/110 |
| 5,750,131 A * | 5/1998 | Wichert et al. ......... 424/422 |
| 6,613,927 B1 | 9/2003 | Kwok |
| 2004/0186074 A1 | 9/2004 | Daftary et al. |
| 2005/0272698 A1 | 12/2005 | Daftary et al. |

FOREIGN PATENT DOCUMENTS

| DE | 195 40 132 | 4/1997 |
| EP | 0 538 858 | 4/1993 |
| EP | 1 396 268 | 3/2004 |
| WO | WO 03/051297 | 6/2003 |

OTHER PUBLICATIONS

The Merck Manual, 12th Edition, 1996, Entry 4937 ("Ifosfamide") at pp. 841-842.*
Japanese Office Action, Japanese Patent Application No. 2006-533996, filed Oct. 18, 2010.
Communication under Rule 71(3) EPC, Minutes of the oral proceedings before the Examining Division, Dec. 21, 2010, Application No. 04 789 095.9-2123.
Ifosfamide—Safety Data Sheet—Division of Occupational Health and Safety National Institutes of Health, 1996.

* cited by examiner

*Primary Examiner* — James D Anderson
(74) *Attorney, Agent, or Firm* — Pillsbury Winthrop Shaw Pittman LLP

(57) ABSTRACT

The invention concerns the use of mercaptoethane sulfonate-sodium (Mesna) to increase the solubility of Ifosfamide in storage-stable, concentrated and/or highly-concentrated (supersaturated) aqueous pharmaceutical preparations, storage-stable, concentrated and/or highly-concentrated (supersaturated) aqueous pharmaceutical Ifosfamide preparations for parenteral administration as well as a process for their production.

10 Claims, No Drawings

SUPERSATURATED AQUEOUS IFOSFAMIDE COMPOSITIONS

This application claims priority from provisional application No. 60/507,750 filed on Oct. 1, 2003.

FIELD OF THE INVENTION

The invention concerns the use of mercaptoethane sulfonate-sodium (Mesna) to increase the solubility of Ifosfamide in storage-stable, concentrated and/or highly-concentrated (supersaturated) aqueous pharmaceutical preparations, storage-stable, concentrated and/or highly-concentrated (supersaturated) aqueous pharmaceutical Ifosfamide preparations for parenteral administration as well as a process for their production.

STATE OF THE ART

Ifosfamide (2-(chlorethylamino)-3-(2-chlorethyl)-tetrahydro-2H-1,3,2-oxazaphosphorin-2-oxide) is an alkylating cytostatic agent that is administered against a variety of tumor-diseases, at times in combination with other cytostatic agents. Mesna (mercaptoethane sulfonate-sodium) is co-administered with Ifosfamide in order to reduce the side-effects of Ifosfamide (c.f. U.S. Pat. Nos. 4,770,870 and 4,220,660; German Patent Application DE 2806866).

The solubility of Ifosfamide in water is limited and at room temperature is a maximum of about 140 mg/mL (saturation concentration). The addition of auxiliary agents can sometimes lower the solubility of Ifosfamide, e.g. to under 10% (wt/vol), so that even at low concentrations, the use of a solubility-enhancing agent is necessary in order to obtain a clear, injectable solution.

A concentrated and/or high-concentrated Ifosfamide solution has critical advantages in handling in comparison to a diluted solution. The dosage of Ifosfamide depends upon the body surface or weight of the patient and lies in general between 3 g and 5 g, but can in individual cases also be over 10 g. For exacting preparation of patient-specific dosage, volumes are advantageous that are easily handled and that can be added to standard infusion solutions. For a concentrated Ifosfamide solution of e.g. 20% (wt/vol) active ingredient, 15 ml to 25 ml will have to be dosed, which allows for a sufficiently highly precise dosage as well as easy handling of single injection. In contrast to this, a currently marketed Ifosfamide solution of 4% (wt/vol) content must be dosed at 75 ml to 125 ml, and in individual cases, as much as 250 ml.

On the basis of the aforementioned limitations of solubility, solutions of Ifosfamide at concentrations >10% (wt/vol) for parenteral use that are devoid of particles and crystals are possible only with the addition of a solubility-enhancing agent. Based on the presentation form as injectable solution, these solubility-enhancing agents must be free from any physiological concerns. In the state of the art, a urea is suggested as solubility-enhancing agent (c.f. WO 99/18973). Urea is, however, suspected to increase the neural side-effects of Ifosfamide.

As solubility-enhancing agents, theoretically Tensides such as, e.g., Tween 80 or Poloxamer can be considered. The ability to use them, however, is limited or in some cases forbidden on account of their haemological characteristics.

For this reason there exists a need for storage-stable concentrated and/or highly concentrated pharmaceutical Ifosfamide preparations that do not require the addition of urea and/or Tensides.

SUMMARY OF THE INVENTION

Surprisingly, it has been found that through the use of mercaptoethane sulfonate-sodium (Mesna) a highly concentrated (supersaturated) aqueous solution of Ifosfamide can be successfully prepared, whose concentration is substantially above the saturation concentration of Ifosfamide in water. The saturation concentration of about 140 mg/ml at room temperature as well as the saturation concentration of about 190 mg/ml at about 5° C. can be surpassed by a wide margin by the use of Mesna. By the use of Mesna as solubility-enhancing agent, a storage-stable concentrate of Ifosfamide can be successfully produced in respect of its physical characteristics in a concentration region from about 10% (wt/vol) to 50% (wt/vol).

Solutions with an Ifosfamide content above the aforementioned amounts and concentrations are hereinafter referred to as highly concentrated and/or supersaturated, whereby the term "supersaturated" means that the preparations according to the invention are storage-stable and free of precipitation of Ifosfamide in spite of the high concentration of Ifosfamide.

The use of Mesna as solubility-enhancing agent in the production of concentrated and/or highly concentrated Ifosfamide solutions is neither described in nor suggested by the state of the art.

The use of Mesna according to the invention enables the production of aqueous concentrates of the active agent Ifosfamide in concentrations above the saturation concentration of Ifosfamide in water, i.e. greater than 10% (wt/vol), using Mesna as a solubility-enhancing agent for Ifosfamide. Preferably, preparations with Ifosfamide concentrations greater than 10% (wt/vol) up to 50% (wt/vol) are formed. At the same time, solution temperatures are selected between 0° C. and 30° C., preferably 2° C. and 20° C., especially preferred 5° C. and 15° C.

The production of concentrates is brought about by dissolving the required amount of Mesna, e.g. 5 g to 50 g per 100 ml, preferably 10 g to 20 g per 100 ml and optionally a suitable buffer (phosphate, borate, carbonate buffer, preferably phosphate buffer) in Water for Injection (WFI), subsequently the corresponding quantity of Ifosfamide is added to a room temperature or preferably cooled solution of Mesna, whereby the ratio of Ifosfamid to Mesna is from 1:0.25 to 1:4, preferably 1:0.5 to 1:2, more preferably 1:0.8 to 1:1.2, most preferably 1:1.0 to 1:1.2. The ratios refer to the proportions by weight of the substances in the solution. The solutions are homogenized, sterilized by filtration and filled under aseptic conditions. Production is carried out under nitrogen. These solutions can also be lyophilized in order to obtain a longer storage life of the pharmaceutical preparation. In addition to the auxiliary agents that are set forth in the examples, the solution can contain also further substances, e.g. sodium chloride, Mannitol, lactose, polyethyleneglycol, ethanol, glucose, disaccharide, cyclodextrine.

The term "cooled" solution temperatures means from about 0° C. to about below room temperature (below about 21° C.), preferably from about 2° C. to lower than or equal to about 20° C., more preferably from about 5° C. to about 15° C., still more preferably from about 5° C. to about 10° C.

The invention will be more specifically demonstrated by the following examples, but should not be restricted to them.

EXAMPLE 1

Ifosfamide Concentrate 20% (Wt/Vol) with 20% (Wt/Vol) Mesna Content

Composition of the Solution:

| | |
|---|---|
| Ifosfamide | 2000.0 mg |
| Mesna | 2000.0 mg |

|  |  |
|---|---|
| Phosphate buffer | 1000.0 mg |
| Water (WFI) | 6540.0 mg |

In the manufacture, 90% of the Water for Injection is cooled to about 5° C. to 10° C., to which is dissolved the phosphate buffer; the Mesna is subsequently added and is homogeneously dissolved. Finally, the Ifosfamide in the solution is dissolved and the pH is set at 7.4 with ortho-phosphoric acid. The solution so obtained is brought to the specified weight with the cooled Water for Injection, sterile-filtered and filled in injection vials under aseptic conditions. Sterilization and filling are not carried out under cooling.

EXAMPLE 2

Ifosfamide Concentrate 20% (Wt/Vol) with 5% (Wt/Vol) Mesna

Composition of the Solution:

|  |  |
|---|---|
| Ifosfamide | 2000.0 mg |
| Mesna | 500.0 mg |
| Phosphate buffer | 1000.0 mg |
| Water (WFI) | 8040.0 mg |

The solution is produced identically according to the procedure of Example 1.

EXAMPLE 3

Ifosfamide Concentrate 20% (Wt/Vol) with 5% (Wt/Vol) Mesna, Lyophilisate and Reconstituion of the Lyophilisate Composition of the Solution Before Filling and After Reconstitution:

|  |  |
|---|---|
| Ifosfamide | 2000.0 mg |
| Mesna | 500.0 mg |
| Mannitol | 500.0 mg |
| Water (WFI) | 8040.0 mg |

In the manufacture, added to about 90% of the Water for Injection that is pre-cooled to about 5° C. to 10° C. is, sequentially, the Mesna, the Ifosfamide and the Mannitol, whereby each is homogenized until a clear solution is obtained. Subsequently, the solution is sterile filtered and filled under aseptic conditions in injection vials to the specified weight for lyophilisation. Lyophilization ensues with a suitable freeze-dry device and lyophilization process, e.g.

|  |  |
|---|---|
| Freezing | 1 hour at −45° C. |
|  | 3.5 hours maintained at −45° C. |
| Main drying | 0.4 mbar, in 1.5 hours from −45° C. to −15° C. |
|  | 0.4 mbar, 120 hours at −15° C. |
| Post drying | 0.4 mbar, increasing over 4 hours to 20° C. |
|  | Max. vacuum, 6 hours at 20° C. |

The injection vials are sealed shut under nitrogen.

Composition of the Lyophilisate:

|  |  |
|---|---|
| Ifosfamide | 2000.0 mg |
| Mesna | 500.0 mg |
| Mannitol | 500.0 mg |

Reconstitution of the Lyophilisate:

For reconstitution, the lyophilisate is mixed with 8 ml Water for Injection or with a suitable infusion solution, e.g. isotonic salt solution, glucose solution for infusion, Ringer lactate solution, etc. so that an approximately 20% (wt/vol) solution of Ifosfamide is formed. This concentrate can then be used by individual dosage as an additive for an infusion preparation. The production of a lyophilisate and its reconstitution can then ensue with the addition of an auxiliary agent, such as Mannitol, glucose, disaccharide or a similar lyophilisate filler known in the art.

EXAMPLE 4

12% (Wt/Vol) Ifosfamide Concentrate with 5% (Wt/Vol) Mesna

|  |  |
|---|---|
| Ifosfamide: | 3 g |
| Mesna: | 1.25 g |
| Water: | 24.5 g |

EXAMPLE 5

25% (Wt/Vol) Ifosfamide Concentrate with 10% (Wt/Vol) Mesna

|  |  |
|---|---|
| Ifosfamide: | 6.25 g |
| Mesna: | 2.5 g |
| Water: | 23.75 g |

EXAMPLE 6

50% (Wt/Vol) Ifosfamide Concentrate with 20% (Wt/Vol) Mesna

|  |  |
|---|---|
| Ifosfamide: | 12.5 g |
| Mesna: | 5.0 g |
| Water: | 17.5 g |

The making of Examples 4, 5 and 6 is carried out analogously to the description of Example 1. The solubility-enhancing properties of Mesna in respect of Ifosfamide are demonstrated over a wide range of concentrations and proportions. The addition of a buffer, e.g. phosphate buffer, largely does not influence the solubility-enhancement, the buffering addition being however necessary for the chemical stabilization of the preparation in order to minimize decomposition of the active agent and in order to obtain sufficient storability of the solution. Apart from that, the Mesna provides as solubility-enhancing agent a physical stabilization that prevents crystallization.

The invention claimed is:

1. A method of preparing an aqueous pharmaceutical preparation comprising a supersaturated Ifosfamide solution, said method comprising:
   a. cooling about 90% of the required amount of buffered water to a temperature of from about 0° C. to 21° C.;
   b. dissolving the required amount of Mesna in the cooled, buffered water;
   c. dissolving an amount of Ifosfamide in said buffered Mesna solution;
   d. adjusting the resulting solution from steps a-c to a pH of from about 6 to about 8;
   e. adding the remaining 10% of the required amount of water to the solution; wherein said required amount of Mesna is at least 5 g/100 ml and up to 50 g/100 ml,
   wherein a final Ifosfamide concentration is greater than 20% (wt/vol.) and up to 50% (wt/vol.), and
   wherein said solution is free of additional solubility-enhancing agents.

2. The method according to claim 1, wherein the weight ratio of Ifosfamide to Mesna is in the range of 1:0.25 to 1:4.

3. The method according to claim 1, wherein the pH is set at pH 6-8 with a phosphate buffer.

4. The method according to claim 1, wherein the water used is at a temperature ranging from 2° C. to 20° C.

5. The process method according to claim 1, wherein one or more auxiliary agents is added entirely or in portions before, during or after the steps a, b, or c.

6. The method according to claim 1, comprising the additional steps of filtering under sterile conditions and filling into suitable containers under aseptic conditions.

7. The method according to claim 4, wherein the water is used at a temperature in the range of 5° C. to about 10-15° C.

8. The method according to claim 5, wherein said auxiliary agent is mannitol.

9. A storage-stabile aqueous pharmaceutical preparation for parenteral administration containing an aqueous, supersaturated Ifosfamide solution in an amount greater than 20% (wt./vol.) and up to 50% (wt./vol.) and Mesna,
   wherein the amount by weight of Ifosfamide and Mesna is in a weight ratio of 1:1 to 4:1, respectively,
   wherein said Ifosfamide is present in an amount greater than 20% (wt./vol.) and up to 50% (wt./vol.), and
   wherein said aqueous pharmaceutical preparation is free of additional solubility-enhancing agents.

10. A storage stable aqueous pharmaceutical preparation according to claim 9, characterized in that the pH is set at pH 6-8 by way of a suitable buffer.

* * * * *